United States Patent [19]

Russell et al.

[11] Patent Number: 4,534,877

[45] Date of Patent: Aug. 13, 1985

[54] SHAMPOO COMPOSITIONS COMPRISING SPECIFIC BETAINE SURFACTANTS AND A QUATERNARY COMPOUND

[75] Inventors: Glen D. Russell, Middletown; Christian Steuri, Fairfield, both of Ohio

[73] Assignee: The Procter & Gamble Company, Cincinnati, Ohio

[21] Appl. No.: 506,921

[22] Filed: Jun. 22, 1983

Related U.S. Application Data

[63] Continuation-in-part of Ser. No. 403,907, Jul. 20, 1982, abandoned.

[51] Int. Cl.³ .................. A61K 7/08; C11D 1/62; C11D 1/90; C11D 3/26
[52] U.S. Cl. .................. 252/106; 252/136; 252/142; 252/542; 252/546; 252/547; 252/DIG. 13; 252/DIG. 14; 424/70
[58] Field of Search ............... 252/136, 142, 542, 546, 252/DIG. 13, 547, DIG. 14, 106; 424/70

[56] References Cited

U.S. PATENT DOCUMENTS

| | | |
|---|---|---|
| 3,328,307 | 6/1967 | Schmitz . |
| 3,496,110 | 2/1970 | Shumway et al. . |
| 3,697,452 | 10/1972 | Olson et al. . |
| 3,755,559 | 8/1973 | Hewitt . |
| 3,822,312 | 7/1974 | Sato et al. . |
| 3,849,348 | 11/1974 | Hewitt . |
| 3,957,970 | 5/1976 | Korkis . |
| 3,990,991 | 11/1976 | Gerstein . |
| 3,996,146 | 12/1976 | Tarasov . |
| 4,075,131 | 2/1978 | Sterling . |
| 4,080,310 | 3/1978 | Ng et al. . |
| 4,132,679 | 1/1979 | Tsutsumi et al. . |
| 4,137,191 | 1/1979 | Lohr . |
| 4,148,762 | 4/1979 | Koch et al. ................. 252/DIG. 13 |
| 4,181,634 | 1/1980 | Kennedy et al. . |
| 4,231,903 | 11/1980 | Lindemann et al. . |
| 4,246,131 | 1/1981 | Lohr ........................ 252/DIG. 13 |
| 4,247,538 | 1/1981 | Barker . |
| 4,294,728 | 10/1981 | Vanlerberghe et al. . |
| 4,329,335 | 5/1982 | Su et al. . |
| 4,374,056 | 2/1983 | Watanabe et al. .......... 252/DIG. 14 |
| 4,375,421 | 3/1983 | Rubin et al. . |
| 4,381,259 | 4/1983 | Homma et al. .................... 252/542 |

FOREIGN PATENT DOCUMENTS

1062392  5/1958  Fed. Rep. of Germany .

OTHER PUBLICATIONS

Marija Tobis: Betaines: Their Properties and Potential Applications as a Function of pH, Hemijska Industrija, 1978, No. 4, pp. 238–241.

*Primary Examiner*—John E. Kittle
*Assistant Examiner*—Mukund J. Shah
*Attorney, Agent, or Firm*—Richard C. Witte; John V. Gorman; Douglas C. Mohl

[57] ABSTRACT

Shampoo compositions comprising a quaternary ammonium compound and an alkylamido betaine wherein the alkyl group is either lauryl, myristyl or a mixture of the two.

14 Claims, No Drawings

SHAMPOO COMPOSITIONS COMPRISING SPECIFIC BETAINE SURFACTANTS AND A QUATERNARY COMPOUND

CROSS REFERENCE TO RELATED APPLICATION

This is a continuation-in-part application of our application filed July 20, 1982 having Ser. No. 403,907, now abandoned.

BACKGROUND ART

The desire to develop products which simultaneously clean and condition hair has long been present. While the desire has long been present, developing such products has presented innumerable problems. Generally the agents which condition hair best are cationic with one or more long fatty hydrocarbon chains. Hair being negatively charged will allow for the cationic portion to attach to the hair while the long fatty chain(s) provide for ease of combing and hair conditioning.

Cationic materials generally cannot be used with good cleaning anionic surfactants and still deliver good hair condition. This meant that other surfactants such as nonionics, amphoterics and zwitterionics were examined by workers in the field. Many of these efforts are reflected in patents issued in the conditioning shampoo area.

U.S. Pat. No. 3,849,348, Nov. 19, 1974 to Hewitt discloses conditioning shampoos containing betaine, cationic and amine oxide surfactants. U.S. Pat. No. 3,697,452, Oct. 10, 1972 to Olson et al discloses shampoo compositions similar to those in Hewitt. Another patent to Hewitt is U.S. Pat. No. 3,755,559, Aug. 28, 1973 disclosing shampoos containing a tertiary amine oxide, a higher alkyl betaine and a soap. U.S. Pat. No. 3,822,312, July 2, 1974 to Sato discloses shampoos containing a quaternary ammonium salt, a betaine and an additional additive. U.S. Pat. No. 3,990,991, Nov. 9, 1961 to Gerstein discloses shampoos containing amphoteric surfactants and quaternary ammonium compounds. U.S. Pat. No. 4,080,310, Mar. 21, 1978 to Ng et al discloses shampoos containing an amphoteric surfactant and a cationic resin. U.S. Pat. No. 4,132,679, Jan. 2, 1979 to Tsutsumi et al discloses shampoos containing a phosphoric acid ester salt and a betaine. U.S. Pat. No. 4,231,903, Nov. 4, 1980 to Lindemann et al discloses shampoos containing a mixture of an amido betaine and a phosphobetaine. U.S. Pat. No. 4,247,538, Jan. 27, 1981 to Barker discloses a conditioning shampoo containing a betaine, a polypropoxylated quaternary ammonium chloride surfactant and gum arabic. U.S. Pat. No. 4,294,728, Oct. 13, 1981 to Vanlergerghe et al discloses shampoos containing a cationic, amphoteric or zwitterionic surfactant and a diol. U.S. Pat. No. 4,329,335, May 11, 1981 to Su et al discloses a shampoo composition containing a betaine, an amine oxide and a polymerized quaternary compound. U.S. Pat. No. 4,181,634, Jan. 1, 1980 to Kennedy et al discloses shampoos containing a betaine and a bisquaternary compound.

While the above described references disclose compositions containing components of the type used in the present compositions, they do not teach or suggest totally satisfactory answers to the questions of good cleaning, conditioning and stability (freeze thaw). It is believed that good cleaning with quaternary compounds is in part dependent on limiting the reacting of the quaternary with the fatty acids in sebum.

In addition the references fail to teach or suggest combining betaine surfactants of the type disclosed herein with quaternary ammonium compounds.

It is, therefore, an object of the present invention to provide hair conditioning shampoo compositions which provide good cleaning and conditioning. The good cleaning relates to improved sebum emulsification as well as good lather.

It is a further object of the present invention to provide shampoo compositions containing particular betaine surfactants and quaternary ammonium compounds.

These and other objects will become more apparent from the detailed description which follows.

Unless otherwise indicated, all percentages and ratios herein are by weight.

DISCLOSURE OF THE INVENTION

The compositions of the present invention comprise from about 5% to 70% of an amido betaine, from about 0.5% to about 10% of a quaternary ammonium or imidazolinium compound, and from about 20% to about 94.5% water.

DETAILED DESCRIPTION OF THE INVENTION

The essential as well as optional components of the present compositions are described in detail below.

Surfactant

The essential surfactants used in the compositions of the present invention are higher alkylamido betaines.

The betaines may be represented by the following structural formula:

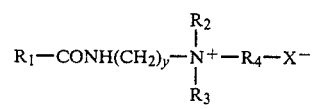

wherein $R_1$ is an alkyl radical having 12 or 14 carbon atoms or a mixture thereof, $R_2$ and $R_3$ are each alkyl radicals having from about 1 to about 3 carbon atoms, $R_4$ is an alkylene or hydroxy alkylene radical having from about 1 to about 4 carbon atoms, y is an integer from 1 to 4, and X is a carboxylate radical. $R_1$ may contain one or more intermediate linkates or non-functional substituents such as hydroxy or halogen radicals which do not affect the hydrophobic character of the radical. Examples of betaines useful herein include myristylamidopropyldimethylcarboxymethyl betaine, laurylamidopropyldimethylcarboxymethyl betaine and blends of these materials. In many instances the dimethylcarboxymethyl part of the designation is not included.

The amount of surfactant is from about 5% to about 70%, preferably from about 10% to about 25%.

Quaternary Compound

The second essential component of the present invention is a quaternary ammonium or imidazolinium salt.

Quaternary ammonium salts can have the formula:

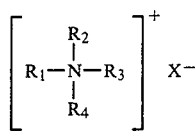

wherein $R_1$ is hydrogen, an aliphatic group of from 1 to 22 carbon atoms, or an aromatic, aryl or alkaryl group having 6 to 20 carbon atoms; $R_2$ is an aliphatic group having from 12 to 22 carbon atoms; $R_3$ and $R_4$ are each alkyl groups having from 1 to 3 carbon atoms; and X is an anion selected from halogen, acetate, phosphate, nitrate and methylsulfate radicals.

Preferred quaternary ammonium salts are the dialkyl-dimethylammonium chlorides, wherein the alkyl groups have from 12 to 22 carbon atoms and are derived from long chain fatty acids, such as tallow or hydrogenated tallow. The term "tallow" refers to fatty alkyl groups derived from tallow fatty acids. Such fatty acids give rise to quaternary compounds wherein $R_1$ and $R_2$ have predominately from 16 to 18 carbon atoms.

Representative examples of quaternary ammonium salts useful in this invention include ditallowdimethylammonium chloride, ditallowdimethylammonium methylsulfate, dihexadecyldimethylammonium chloride, di(hydrogenated tallow)dimethylammonium chloride, dioctadecyldimethylammonium chloride, dieicosyldimethylammonium chloride; didocosyldimethylammonium chloride, di(hydrogenated tallow)dimethylammonium acetate, dihexadecyldiethylammonium chloride, dihexadecyldimethylammonium acetate, ditallowdipropylammonium phosphate, ditallowdimethylammonium nitrate, di(coconutalkyl)dimethylammonium chloride; cetyltrimethylammonium chloride and stearyldimethylbenzylammonium chloride.

Other quaternary ammonium salts useful herein are the compounds of the formula:

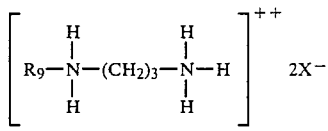

wherein $R_9$ is an aliphatic group having 16 to 22 carbon atoms and X is an anion as above defined. Tallow-propanediamine hydrochloride is an example of this quaternary ammonium salt.

Quaternary imidazolinium salts have the formula:

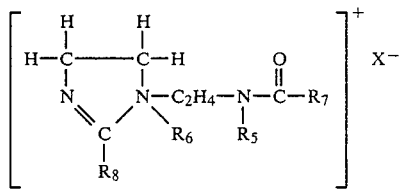

wherein $R_6$ is an alkyl group containing from 1 to 4, preferably from 1 to 2, carbon atoms; $R_5$ is an alkyl group containing from 1 to 4 carbon atoms; or a hydrogen atom; $R_8$ is an alkyl group containing from 1 to 22, preferably at least 15 carbon atoms, or a hydrogen atom; $R_7$ is an alkyl group containing from 8 to 22, preferably at least 15, carbon atoms; and X is an anion, preferably chloride. Other suitable anions include those disclosed with reference to the quaternary ammonium salts described hereinbefore.

Particularly preferred are those imidazolinium salts in which both $R_7$ and $R_8$ are alkyl of from 12 to 22 carbon atoms, e.g., 1-methyl-1-[(stearoylamide)ethyl]-2-heptadecyl-4,5-dihydroimidazolinium chloride; 1-methyl-1-[(palmitoylamide)ethyl]-2-octadecyl-4,5-dihydroimidazolinium chloride; and 1-methyl-1-[(tallowamide)-ethyl]-2-tallow-imidazolinium methylsulfate.

The quaternary salt is present at a level of from about 0.5% to about 10%, preferably from about 1% to about 6%.

Water

Water is the last essential component of the present invention and forms the remainder of the composition. It is generally present at a level of from about 20% to about 94.5%, preferably from about 65% to about 80%.

Optional Components

The shampoos herein can contain a variety of non-essential, optional components suitable for rendering such compositions more stable and desirable. Such conventional optional ingredients are well known to those skilled in the art, e.g., preservatives such as benzyl alcohol, methyl paraben, propyl paraben and imidazolidinyl urea; betaine surfactants such as lauryl betaine in an amount up to about equal to the amount of the amidobetaine; thickeners and viscosity modifiers such as a diethanolamide of a long chain fatty acid (e.g., coconut diethanolamide), sodium chloride, sodium sulfate, methylcellulose, polyvinyl alcohol, and ethyl alcohol; pH adjusting agents such as citric acid, succinic acid, phosphoric acid, sodium hydroxide, sodium carbonate, etc.; suspending agents such as hydrogenated castor oil; opacifiers such as ethylene glycol distearate; perfumes; dyes; and, sequestering agents such as disodium ethylenediamine tetraacetate. Such agents, except for the betaine surfactants, generally are used individually at a level of from about 0.01% to about 10% by weight of the compositions. The pH of the instant compositions is from about 2.5 to about 9, preferably from about 3 to about 6.5.

METHOD OF MANUFACTURE

The shampoos of the present invention may be made in a variety of ways. A preferred method is set forth in Example I.

INDUSTRIAL APPLICABILITY

The present compositions are used in a conventional manner for cleaning hair. From about 0.1 g to about 10 g of the composition is applied to hair that has been wetted, generally with water, worked through the hair and then rinsed out.

The following Examples further describe and demonstrate the preferred embodiments within the scope of the present invention. The Examples are given solely for the purpose of illustration and are not to be construed as limitations of the present invention as many variations thereof are possible without departing from its spirit and scope.

EXAMPLE I

The following composition was prepared and is representative of the present invention (all %'s are on a 100% active basis):

| Component | Wt. % |
|---|---|
| Mirataine BB[1] | 18.0 |
| Variquat E228[2] | 4.0 |
| Citric Acid | 4.0 |
| Clindrol Superamide[3] 100 CG | 4.5 |
| Water, perfume, dye and Preservative | 100.00% q.s. |

[1]Lauramidopropyl betaine supplied by Miranol Chemical Company.
[2]Cetrimonium chloride supplied by Sherex Chemical Company.
[3]Cocamide diethanol amide supplied by Clintwood Chemical Company.

Preparation of Example I

The water, betaine and quaternary ammonium compound are mixed together with agitation and heat. Citric acid is then added. When the temperature reaches about 150° F. the cocamide DEA is added and the temperature is increased to the 150° F. to 160° F. range. The batch is kept at 150° F.–160° F. until it is clear. The remaining ingredients are then added.

EXAMPLE II

The following three compositions were prepared to test for ability to withstand a freeze thaw test.

| Component | Wt. Percent | | |
|---|---|---|---|
|  | A | B | C |
| Aersol 30[1] | 18 | — | — |
| Mirataine BB | — | 18 | — |
| Tetradecamidopropyl betaine | — | — | 18 |
| Clindrol Superamide 100 CG | 2.5 | → | → |
| Adogen 470 DE[2] | 4.0 | → | → |
| Water, perfume, dye and Preservative | 100% q.s. | → | → |

[1]Cocamido propyl betaine supplied by American Cyanamid.
[2]Ditallowdimonium chloride supplied by Sherex Chemical Company.

When these compositions were subjected to 0° F. to freeze them and then brought to room temperature (75° F.) only compositions B and C, representative of this invention, remained clear. Composition A had white particulate matter evenly dispersed in about 75% of the sample.

What is claimed is:

1. A shampoo composition having good freeze-thaw stability consisting essentially of:
   (a) from about 0.5% to about 10% of a hair conditioning agent selected from the group consisting of quaternary ammonium compounds and quaternary amidazolinium compounds;
   (b) from about 5% to about 25% of a higher alkylamido betaine, wherein the alkyl group is selected from the group consisting of lauryl, myristyl and mixtures thereof; and
   (c) the remainder water.

2. A shampoo composition according to claim 1 wherein component(A) is a quaternary ammonium compound and is present at a level of from about 1% to about 6%.

3. A shampoo composition according to claim 2 wherein the quaternary compound is a dialkyldimethylammonium salt.

4. A shampoo composition according to claim 3 wherein the higher alkylamido betaine is a higher alkylamidopropyl dimethylcarboxymethyl betaine.

5. A shampoo composition according to claim 4 which in addition contains a diethanolamide of a long chain fatty acid.

6. A shampoo composition according to claim 5 wherein the higher alkylamido betaine is laurylamidopropyldimethylcarboxymethyl betaine.

7. A shampoo composition according to claim 6 wherein the quaternary compound is ditallowdimethylammonium chloride.

8. A shampoo composition according to claim 5 wherein the higher alkylamido betaine is myristylamidopropyldimethylcarboxymethyl betaine.

9. A shampoo composition according to claim 8 wherein the quaternary compound is ditallowdimethylammonium chloride.

10. A method of cleaning hair comprising:
    (a) applying from about 0.1 g to about 10 g of a composition according to claim 1 to hair that has been wetted;
    (b) working said composition through said hair; and
    (c) rinsing said composition from said hair.

11. A method according to claim 10 wherein said composition is in accordance with claim 3.

12. A method according to claim 10 wherein said composition is in accordance with claim 4.

13. A method according to claim 10 wherein said composition is in accordance with claim 6.

14. A method according to claim 10 wherein said composition is in accordance with claim 8.

* * * * *